United States Patent
Brown et al.

[11] Patent Number: 6,059,810
[45] Date of Patent: May 9, 2000

[54] ENDOVASCULAR STENT AND METHOD

[75] Inventors: Brian J. Brown, Hanover; Paul H. Burmeister, Maple Grove; Charles L. Euteneuer, St. Michael, all of Minn.

[73] Assignee: SciMed Life Systems, Inc., Maple Grove, Minn.

[21] Appl. No.: 08/789,738

[22] Filed: Jan. 27, 1997

Related U.S. Application Data

[63] Continuation of application No. 08/438,253, May 10, 1995, abandoned.

[51] Int. Cl.$^7$ .................................................. A61M 29/00
[52] U.S. Cl. ...................... 606/198; 606/198; 606/195; 606/192; 623/1; 623/12; 128/342; 128/343; 128/745
[58] Field of Search .................... 606/198, 195, 606/192; 623/1, 12; 128/342, 343, 745

[56] References Cited

U.S. PATENT DOCUMENTS

| | | |
|---|---|---|
| 3,868,956 | 3/1975 | Alfidi et al. . |
| 4,503,569 | 3/1985 | Dotter . |
| 4,512,338 | 4/1985 | Balko et al. . |
| 4,733,665 | 3/1988 | Palmaz . |
| 4,950,227 | 8/1990 | Savin et al. . |
| 4,950,258 | 8/1990 | Kawai et al. . |
| 4,969,890 | 11/1990 | Sugita et al. ............................ 606/192 |
| 5,019,090 | 5/1991 | Pinchuk . |
| 5,037,427 | 8/1991 | Harada et al. . |
| 5,092,877 | 3/1992 | Pinchuk . |
| 5,102,417 | 4/1992 | Palmaz . |
| 5,104,404 | 4/1992 | Wolff . |
| 5,114,504 | 5/1992 | Judom, II et al. ...................... 148/402 |
| 5,133,732 | 7/1992 | Wiktor . |
| 5,135,536 | 8/1992 | Hillstead . |
| 5,195,984 | 3/1993 | Schatz ..................................... 606/195 |
| 5,197,978 | 3/1993 | Hess ............................................ 623/1 |
| 5,242,451 | 9/1993 | Harada et al. . |
| 5,545,210 | 8/1996 | Hess et al. . |

FOREIGN PATENT DOCUMENTS

| | | |
|---|---|---|
| 0 380 666 A1 | 4/1989 | European Pat. Off. . |
| 0 364 787 A1 | 4/1990 | European Pat. Off. . |
| 0 606 165 A1 | 7/1994 | European Pat. Off. . |
| 2 617 721 | 1/1989 | France . |
| WO92/19310 | 11/1992 | WIPO . |
| WO93/08767 | 5/1993 | WIPO . |
| WO94/20044 | 9/1994 | WIPO . |
| WO96/09020 | 3/1996 | WIPO . |

OTHER PUBLICATIONS

Article by L. McDonald Schetky entitled "Shape–Memory Alloys", at pp. 74–82, vol. 241, No. 5, Nov. 1979, *Scientific American*.

Publication entitled "*A Source Manual for Information on NItinol and Ni Ti*", First Revision, by David Goldstein, Research and Technology Department, Feb. 1, 1980, Naval Surface Weapons Center, Dalgren, Virginia 22448 (NSWC TR 80–59).

*Primary Examiner*—Michael Buiz
*Assistant Examiner*—Kevin Truong
*Attorney, Agent, or Firm*—Vidas, Arrett & Steinkraus, P.A.

[57] ABSTRACT

A stent for reinforcing a vessel wall is disclosed, the stent being expandable and comprised of a shape memory alloy which in the normal implanted condition is in the martensitic phase at body temperature, the stent further having a larger parent or austenitic shape and diameter when heated above its transition temperature.

10 Claims, 3 Drawing Sheets

ENDOVASCULAR STENT AND METHOD

This application is a continuation of Ser. No. 08/438,253 filed May 10, 1995, abandoned.

TECHNICAL FIELD

The present invention relates to an endo-prosthesis device for implantation within a body vessel, duct or the like, typically a blood vessel.

BACKGROUND OF THE INVENTION

A type of endo-prosthesis device, commonly referred to as a stent, is placed or implanted within a blood vessel for treating stenoses, strictures or aneurysms and the like in the blood vessel. These devices are implanted within the vascular system to reinforce collapsing, partially occluded, weakened, or abnormally dilated sections of the blood vessel. Stents also have been successfully implanted in the urinary tract or the bile ducts to reinforce those body vessels.

The present invention generally relates to stents and to the use thereof. Such stents are generally tubular in configuration, are open ended, and are radially expandable between a generally unexpanded insertion diameter and an expanded implantation diameter which is greater than the unexpanded insertion diameter. Such intravascular implants are used for maintaining vascular patency in both humans and animals.

Stents are typically placed or implanted by a mechanical transluminal procedure. One common procedure for implanting a stent is to first open the region of the vessel with a balloon catheter and then place the stent in a position that bridges the weakened portion of the vessel. Prior art patents refer to the construction and design of stents as well as apparatus for positioning stents within a vessel. In general, such patents disclose a technique for positioning an elongated cylindrical stent at selected regions in a vessel. The stent expands to an implanted configuration after insertion with the aid of a catheter.

Specifically, U.S. Pat. No. 4,733,665 to Palmaz which issued Mar. 29, 1988, discloses a number of stent configurations for implantation with the aid of a catheter. The catheter includes means for mounting and retaining the stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel. U.S. Pat. No. 4,950,227 to Savin et al., which issued on Aug. 21, 1990 is similar.

Another similar U.S. Pat. No. 5,019,090 discloses a generally cylindrical stent and a technique for implanting it using a deflated balloon catheter to position the stent within a vessel. Once the stent is properly positioned the balloon is inflated to press the stent against the inner wall linings of the vessel. The balloon is then deflated and withdrawn from the vessel, leaving the stent in place. A patent to Dotter, U.S. Pat. No. 4,503,569 which issued Mar. 12, 1985 discloses a spring stent which expands to an implanted configuration with a change in temperature. The spring stent is implanted in a coiled orientation and heated to cause the spring to expand due to the characteristics of the shape memory alloy from which the stent is made. Similarly, U.S. Pat. No. 4,512,338 to Balko et al., which issued Apr. 23, 1985, discloses a shape memory alloy stent and method for its delivery and use.

Another stent of interest and to which this invention is applicable is described in U.S. patent application Ser. No. 08/246,320, filed May 19, 1994, the entire contents of which is incorporated herein by reference.

All of the above-identified patents are incorporated herein by reference.

It should be understood that the following disclosure is not intended to be exclusive and that any body vessel which has been narrowed, weakened or in any other way requires a reinforcement may be subject to the present invention. Also, as utilized herein, the term vessel is used in a generic sense to include body channels including but not limited to, artery, vein, esophagus, bile duct, urethra, trachea, and the like and that the term body includes not only humans but animals as well. The stent configuration may vary widely from that disclosed.

SUMMARY OF THE INVENTION

The invention makes use of an expandable stent comprised of a shape memory alloy such as Nitinol (nickel titanium). Nitinol generally exists in one of two states or phases 1) austenite or superelastic and 2) martensite. In this invention, the alloy will be primarily comprised of martensite which is a relatively soft deformable material. When a stent is constructed using martensite it can be expanded, as by a balloon or other mechanical means, from its delivered diameter to its deployed diameter and it will behave very similar to other non-shape memory alloys commonly used for expandable stents, such as stainless steel.

The unique feature of the invention associates with using a shape memory alloy in the martensite phase is that, the parent shape and size of the stent is set at the largest diameter of the stent. The stent is then mechanically compressed to an unexpanded insertion diameter and mounted onto an expansion catheter. The stent is implanted by positioning it within the vessel and monitoring its position on a viewing monitor. Once the stent is properly positioned, the catheter is expanded and the stent separated from the catheter body. The catheter can then be withdrawn from the subject, leaving the stent in place within the vessel. After mechanical expansion in the martensite phase, additional expansion may be provided if desired by supplying a source of heat to the shape memory alloy stent, such as by a warm solution, causing a phase change to austenite.

The additional expansion by phase change to austenite can be of benefit in a number of ways:

At the time of initial deployment if additional expansion diameter or force is required beyond that provided by the balloon, a heat source can be applied to the stent causing a phase change to austenite and hence to the larger parent shape and size. This eliminates the need for an additional balloon of larger diameter.

If an abrupt vessel closure or trauma induced closure happens on the stent and a balloon cannot be inserted into the stent, a heat source can be applied to the stent and the stent will reopen the vessel.

During a follow-up angiogram, if restenosis is present at the stent site, additional expansion of the stent may be accomplished by injecting warm saline or the like through the vessel.

During some balloon expandable stent procedures, stents have been known to "watermelon seed" or slide off the balloon during expansion. In such a case with the present type of stent, a warm solution such as saline may be released to cause the stent to self-expand.

If the expander balloon bursts, heated saline can be used to expand the stent.

The shape memory alloy used in the present invention has a transformation temperature above body temperature, i.e., 37° C. Thus, it is unlikely that such a stent would inadvertently be heated thus transforming from the martensite phase to the austenite phase and expanding beyond its normal martensite diameter when not desired. A stent made of such a shape memory alloy can thus be balloon expanded or otherwise expanded in the martensite phase and used similarly to those non-shape memory expandable stents known in the prior art such as those made of stainless steel.

DETAILED DESCRIPTION OF THE INVENTION

Figure 1A:
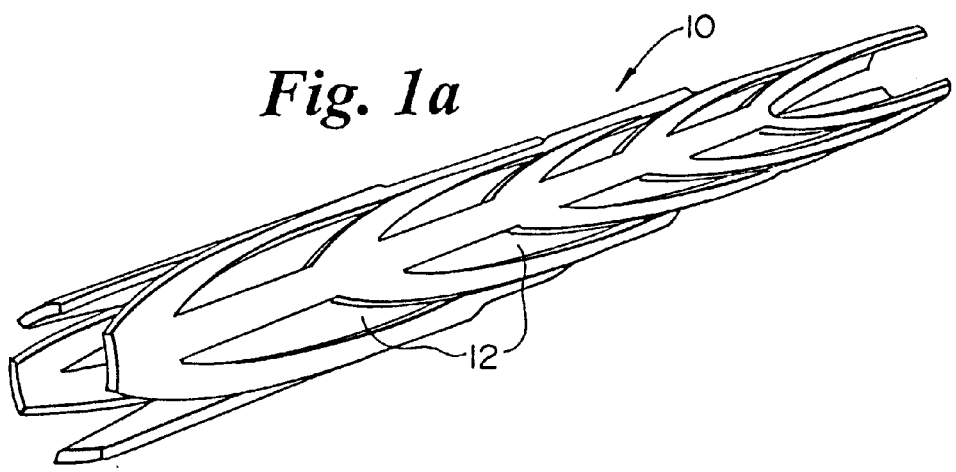
FIGS. 1a and 1b are perspective views of an unexpanded stent and an expanded stent, respectively, according to the invention.

For the purposes of promoting and understanding the principles of the invention, reference will now be made to the embodiment illustrated in the drawing. Figures and specific language will be used to describe the same. It will nevertheless be understood that no limitation of the scope of the invention is thereby intended, such alterations and further modifications in the illustrated device, and such further applications of the principles of the invention is illustrated herein being contemplated as would normally occur to one skilled in the art to which the invention relates. Actual stent configuration may vary widely.

Figure 1B:
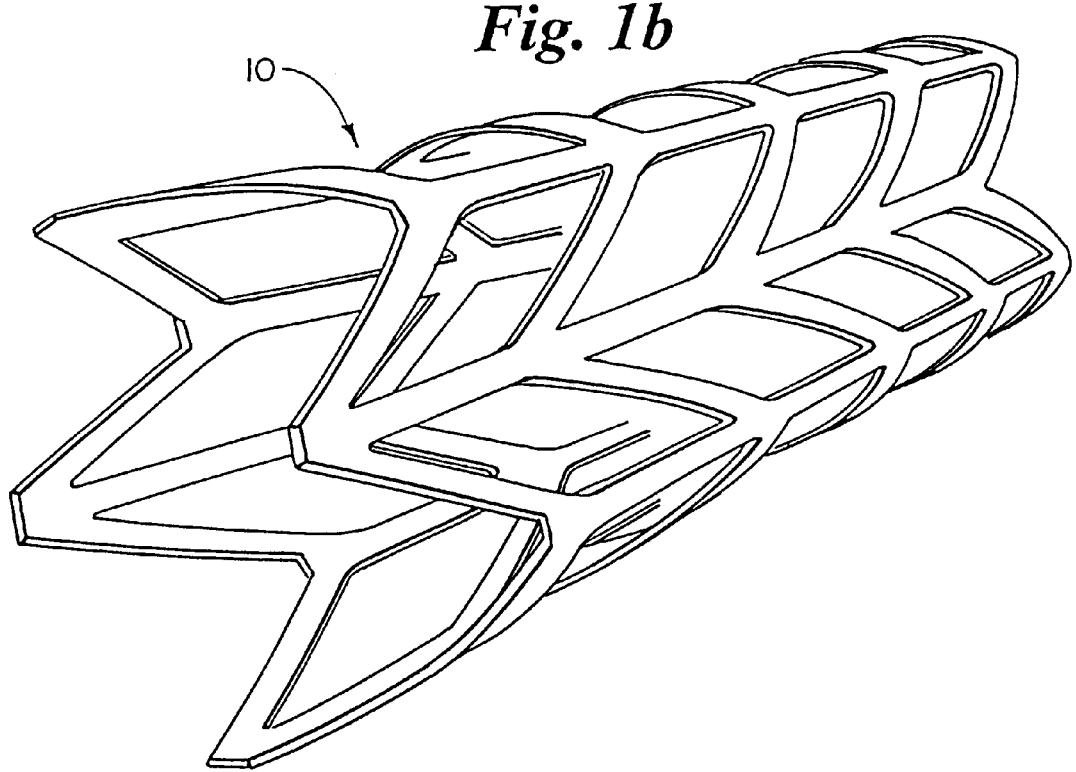

Referring now to the drawing, FIGS. 1a and 1b show a balloon expandable stent according to the present invention generally designated at 10. Stent 10 is a generally tubular shaped, thin walled member having a plurality of longitudinal slots 12 formed therein. Slots 12 are generally aligned with each other and generally aligned with the longitudinal axis of the stent as shown to facilitate its expansion to a configuration such as that shown in FIG. 1b. As can be seen in comparing the slots 12 in FIGS. 1a and 1b, upon expansion by a radially outward force of a balloon or other expander means inserted within the stent, slots 12, (which are initially disposed substantially aligned with the longitudinal axis of the stent as seen in FIG. 1a) are deformed upon stent expansion to a different opened configuration as seen in FIG. 1b.

Figure 2A:
FIGS. 2a and 2b are views of an unexpanded and expanded stent, respectively, of another configuration.
Figure 2B:
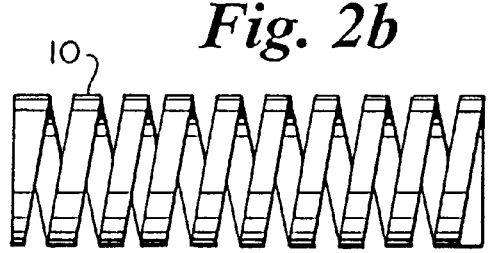
Figure 3A:
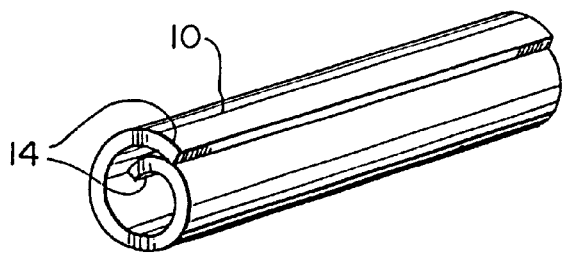
FIGS. 3a and 3b are views of an unexpanded and expanded stent respectively, of yet another configuration.
Figure 3B:
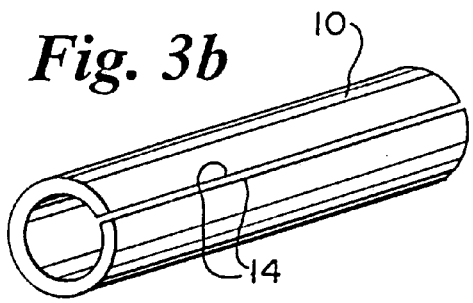
Figure 4A:
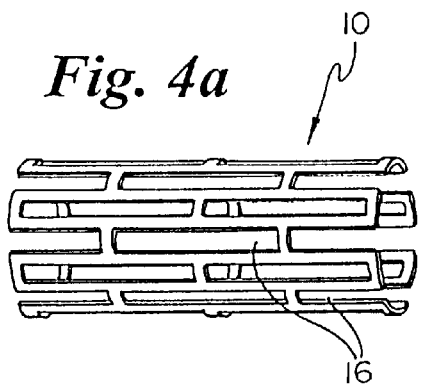
FIGS. 4a and 4b are views of an unexpanded and expanded stent, respectively, of still another configuration.
Figure 4B:
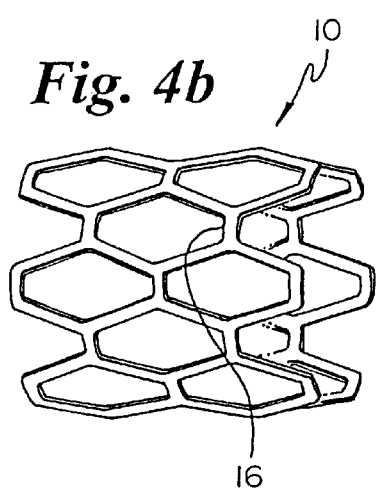

FIGS. 2a and 2b show a stent 10 in the form of an expandable coil. FIGS. 3a and 3b show a stent 10 in the form of a rolled tube with overlapping edges 14 which move apart upon expansion. FIGS. 4a and 4b show a stent with elongated slots 16 which become diamond shaped upon expansion. These various configurations are included to demonstrate the application of the invention to a variety of stent configurations.

Figure 5:
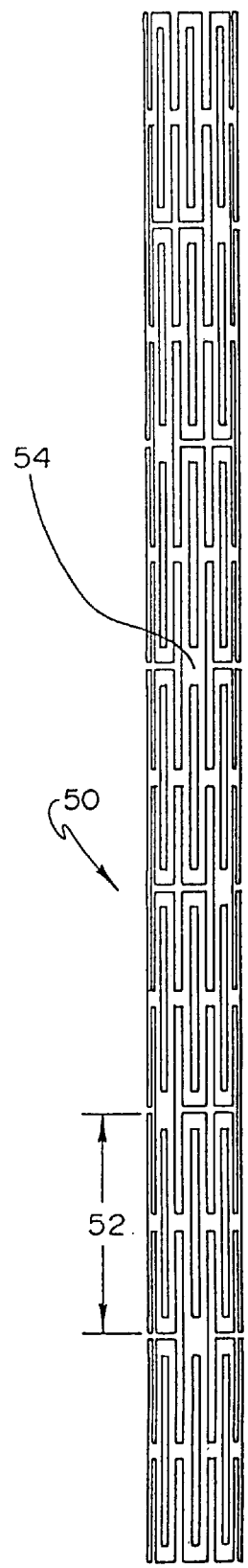
FIG. 5 is a side view of an unexpanded elongated multi-section stent according to the invention, designed for flexibility and extended length.

Referring now to FIG. 5, an expandable intraluminal vascular stent or prosthesis is generally indicated at 50 in a flexible configuration. Such a prosthesis is desirable for implantation in curved body passageways or for use in elongated sections of body passageways when a stent is required which is longer than the stents shown in FIGS. 1–4.

As seen in FIG. 5, stent 50 generally includes a plurality of sections 52. Disposed between adjacent sections 52 are connector members 54 which are evenly spaced around the perimeter of the stent and most preferably are staggered along the length. Connector members 54 flexibly connect adjacent sections 52 of stent 50 and are preferably formed of the same material as the stent per se as previously described and are preferably formed integrally between adjacent sections.

The tubular body of the stents in all configurations is of a shape memory alloy such as Nitinol which exhibits anthropomorphic qualities of memory and trainability. Such alloys are commonly referred to as shape memory alloys. If such alloys are plastically deformed at one temperature, they will recover to their original shape on being raised to a higher temperature. A discussion and identification of such alloys is set forth in the article by L. McDonald Schetky entitled "Shape-Memory Alloys" at pp 74–82 of Volume 241 (5) November 1979, *SCIENTIFIC AMERICAN,* this article being incorporated into the specification by specific reference thereto. A further discussion of such alloys and particularly nickel/titanium alloys commonly referred to as Nitinol is set forth in the publication "A Source Manual For Information On Nitinol and Ni Ti", first revision, by David Goldstein, Research and Technology Department, Feb. 1, 1980, Naval Surface Weapons Center, Dalgren, Va. 22448 (NSWC TR 80-59), specifically incorporated into this specification by specific reference thereto.

In the present invention, Nitinol is shaped by known techniques into a stent form, generally an open-ended cylinder or tube. The diameter of the tube is preferably such that it is smaller than the normal diameter of the vessel into which it is to be implanted but large enough to be readily balloon expandable to a desired implantable size. An alternative method to fabricate the stent is to shape the stent in a tube that is the largest diameter of the stent, or of some iteration between the insertion and the largest diameter of the stent. It is then compressed such that it is smaller than the normal diameter of the vessel into which it is to be implanted. The stent, once balloon expanded, remains in such condition while maintained at a temperature below its martensite transformation temperature, for example approximately 37°.

Again, under normal circumstances, a stent of the invention will exist in the implanted condition in the martensite phase. If, for some reason as already pointed out hereinabove, a larger diameter configuration of the stent is necessary, it may then be supplementally used with the application of heat to transform it above its transformation temperature to the austenite phase or condition and to a further enlarged diameter without the need for additional mechanical expansion, as by a balloon or the like. Of course, this is only possible if the balloon expanded diameter is less than high temperature shape diameter of the stent.

Shape memory materials other than metal alloys may also be used according to the invention. For example, plastic molded articles having characteristic properties of shape memory and even simultaneous biodegradability are available as materials from which stents may be made. For example, see U.S. Pat. No. 4,950,258 to Kawai et al., issued Aug. 21, 1990 for materials which can be made into stent like configurations of a plastic nature and utilized according to this invention. This patent is incorporated in its entirety herein by reference.

The delivery and expansion of the stents of the invention is the same as that already known in the art. U.S. Pat. No. 5,195,984 to Schatz, issued Mar. 23, 1993, describes a typical balloon expansion procedure for an expandable stent. This patent is incorporated in its entirety herein by reference. That patent describes a catheter having an expandable inflatable portion associated therewith. In a conventional manner, the catheter and stent are delivered to a desired location within a body passageway at which it is desired to expand the stent for implantation. Fluoroscopy, and or other conventional techniques may be utilized to insure that the catheter and stent are delivered to the desired location. The stent is then controllably expanded and deformed by controllably expanding the expandable inflatable portion of catheter, typically a balloon. As a result the stent is deformed radially outwardly into contact with the walls of the body passageway. In this regard, the expandable inflatable portion of the catheter may be a conventional angioplasty balloon as is already known in the art. After the desired expansion and deformation of the stent has been accomplished, the angioplasty balloon may be deflated and the catheter removed in a conventional manner from the passageway.

The stents of the invention may be coated with a variety of materials such as polymers, hydrogels, collagen and the like for a variety of reasons. Collagen is a preferred coating. PTFE may also be used.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

Having described the invention, what is claimed is as follows:

1. A balloon-expandable stent mounted on a balloon for mechanical expansion, said stent being comprised of a shape memory alloy in which the normal implanted phase is the martensitic phase at body temperature, the stent having a higher temperature shape (austenitic phase) of the alloy set at a larger diameter than that of the martensitic phase of the stent.

2. The stent of claim 1 comprised of Nitinol alloy.

3. The stent of claim 1 constructed of a plurality of repeating longitudinal sections interconnected by at least one connecting piece for longitudinal flexibility.

4. The stent of claim 3 wherein the positions of the connecting pieces are staggered around the perimeter of the stent along its length.

5. The stent of claim 1 wherein the stent is comprised of a shape memory plastic.

6. A method of permanently implanting a stent in a body passageway, comprising the steps:

providing a generally cylindrical stent mounted on a catheter for mechanical expansion, said stent being comprised of a shape memory alloy in martensitic phase at body temperature and wherein the high temperature shape of the alloy is set at a larger diameter than the martensitic shape, placing the stent in a body passageway, mechanically expanding the stent while in the martensitic state by means of a catheter having an expandable portion, and removing the catheter.

7. The method of claim 6 wherein further expansion of the stent is accomplished by heating it above its transformation temperature to the austenitic phase.

8. The method of claim 6 wherein the stent provided is comprised of Nitinol alloy.

9. A balloon-expandable stent mounted on a balloon for mechanical expansion, said stent being comprised of a shape memory alloy having a martensitic phase and an austenitic phase, the austenitic phase being at a higher temperature than the martensitic phase, wherein the stent is implanted and mechanically expanded by the balloon while in the martensitic phase, the normal implanted phase of the stent at body temperature is the martensitic phase of the alloy, the stent having a higher temperature shape in the austenitic phase of the alloy set at a larger diameter than the diameter of the stent in the martensitic phase of the stent.

10. A method of permanently implanting a stent in a body passageway, said method comprising the steps of:

(a) providing a generally cylindrical stent mounted on a catheter for mechanical expansion, said stent being comprised of a shape memory alloy in the martensitic phase at body temperature and wherein the high temperature shape of the alloy is set at a larger diameter than the martensitic shape;

(b) placing the stent in a body passageway;

(c) expanding the stent, said expansion step consisting of mechanically expanding the stent while in the martensitic state by means of a catheter having an expandable portion, the stent being in the martensitic phase prior to, during and following completion of said expansion step; and (d) removing the catheter;

whereby the stent is permanently implanted in said body passageway while in the martensitic phase.

* * * * *